(12) United States Patent
Mura et al.

(10) Patent No.: US 6,190,852 B1
(45) Date of Patent: *Feb. 20, 2001

(54) PHOTOGRAPHIC ELEMENT CONTAINING NITROGEN HETEROCYCLE SUBSTITUTED CYAN COUPLER AND PROCESS

(75) Inventors: Albert J. Mura; Raymond P. Scaringe; John W. Harder, all of Rochester, NY (US)

(73) Assignee: Eastman Kodak Company, Rochester, NY (US)

( * ) Notice: Under 35 U.S.C. 154(b), the term of this patent shall be extended for 0 days.

This patent is subject to a terminal disclaimer.

(21) Appl. No.: 09/473,931

(22) Filed: Dec. 28, 1999

(51) Int. Cl.⁷ .............................. G03C 1/08; G03C 7/26; G03C 7/32
(52) U.S. Cl. ........................ 430/553; 430/552; 430/384; 430/385
(58) Field of Search .................... 430/552, 553, 430/384, 385

(56) References Cited

U.S. PATENT DOCUMENTS

| | | |
|---|---|---|
| 4,609,619 | 9/1986 | Katoh et al. . |
| 4,775,616 | 10/1988 | Kilminster et al. . |
| 4,849,328 | 7/1989 | Hoke et al. . |
| 5,008,180 | 4/1991 | Merkel et al. . |
| 5,045,442 | 9/1991 | Hoke . |
| 5,183,729 | 2/1993 | Naito et al. . |
| 5,378,596 | 1/1995 | Naruse et al. . |
| 5,674,666 * | 10/1997 | Lau et al. ............... 430/384 |
| 5,681,690 | 10/1997 | Tang et al. . |
| 5,686,235 | 11/1997 | Lau et al. . |
| 5,888,716 * | 10/1999 | Edwards et al. .............. 430/549 |
| 5,962,198 * | 10/1999 | Lau et al. ............... 430/553 |
| 6,048,674 * | 10/1999 | McInerney et al. .............. 430/384 |

FOREIGN PATENT DOCUMENTS

59/111645   6/1984   (JP) .

OTHER PUBLICATIONS

JO 2035–450–A—Konica—Abstract—Feb. 6, 1990.
JO 1253–742–A—Konica—Abstract—Oct. 11, 1989.
JP 04163448–A—Konica—Abstract–Jun. 9, 1992.
JP 04212152–A—Fuji—Abstract—Aug. 3, 1992.
J5 9111–645–A—Konishiroku—Abstract.

\* cited by examiner

*Primary Examiner*—Geraldine Letscher
(74) *Attorney, Agent, or Firm*—Arthur E. Kluegel

(57) ABSTRACT

Disclosed is a photographic element comprising a light-sensitive silver halide emulsion layer having associated therewith a cyan dye-forming coupler represented by Formula (I):

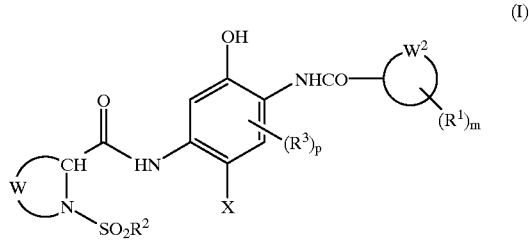

wherein:
each $R^1$ and $R^3$ is an independently selected substituent, m is 0 to 5, and p is 0 to 2;
X is hydrogen or a coupling-off group;
W and $W^2$ represent the atoms necessary to complete rings; and
$R^2$ is an alkyl or aryl group.
The element provides desirable hue properties and ease of synthesis.

20 Claims, No Drawings

PHOTOGRAPHIC ELEMENT CONTAINING NITROGEN HETEROCYCLE SUBSTITUTED CYAN COUPLER AND PROCESS

FIELD OF THE INVENTION

The present invention relates to a color photographic silver halide element containing a particular phenolic cyan coupler containing a nitrogen heterocycle. The coupler provides a desirably narrow spectrographic absorption curve.

BACKGROUND OF THE INVENTION

In silver halide based color photography, a typical photographic element contains multiple layers of light-sensitive photographic silver halide emulsions coated on a support with one or more of these layers being spectrally sensitized to each of blue light, green light and red light. The blue, green, and red light-sensitive layers typically contain yellow, magenta, and cyan dye-forming couplers, respectively. After exposure to light, color development is accomplished by immersing the exposed material in an aqueous alkaline solution containing an aromatic primary amine color-developing compound. The dye-forming couplers are selected so as to react with the oxidized color developing agent to provide yellow, magenta and cyan dyes in the so called subtractive color process to reproduce their complementary colors, blue, green and red as in the original image.

The important features for selecting the dye-forming coupler include: efficient reaction with oxidized color developing agent, thus minimizing the necessary amounts of coupler and silver halide in the photographic element; formation of dyes with hues appropriate for the photographic use of interest (for color photographic paper applications this requires that dyes have low unwanted side absorption leading to good color reproduction in the photographic print); minimization of image dye loss contributing to improved image permanence under both ambient illumination and conventional storage conditions; and, in addition, low crystallization tendency, and thus good solubility in coupler solvents and good dispersibility in gelatin during handling and manipulation for improved efficiency in manufacturing processes.

In recent years, a great deal of study has been conducted to improve dye-forming couplers for silver halide photosensitive materials in terms of improved color reproducibility and image dye stability. However, further improvements are needed, particularly in the area of cyan couplers. In general, cyan dyes are formed from naphthols and phenols as described, for example, in U.S. Pat. Nos. 2,367,351, 2,423, 730, 2,474,293, 2,772,161, 2,772,162, 2,895,826, 2,920,961, 3,002,836, 3,466,622, 3,476,563, 3,552,962, 3,758,308, 3,779,763, 3,839,044, 3,880,661, 3,998,642, 4,333,999, 4,990,436, 4,960,685, and 5,476,757; in French patents 1,478,188 and 1,479,043; and in British patent 2,070,000. These types of couplers can be used either by being incorporated in the photographic silver halide emulsion layers or externally in the processing baths. In the former case the couplers must have ballast substituents built into the molecule to prevent the couplers from migrating from one layer into another. Although these couplers have been used extensively in color photographic film and paper products, the dyes derived from them still suffer from poor stability to heat, humidity or light, low coupling efficiency or optical density, and in particular from undesirable blue and green absorptions which cause considerable reduction in color reproduction and color saturation.

Cyan couplers which have been recently proposed to overcome some of these problems are 2,5-diacylaminophenols containing a sulfone, sulfonamido or sulfate moiety in the ballasts at the 5-position, as disclosed in U.S. Pat. Nos. 4,609,619, 4,775,616, 4,849,328, 5,008, 180, 5,045,442, and 5,183,729; and Japanese patent applications JP02035450 A2, JP01253742 A2, JP04163448 A2, JP04212152 A2, and JP05204110 A2. Even though cyan image dyes formed from these couplers show improved stability to heat and humidity, enhanced optical density and resistance to reduction by ferrous ions in the bleach bath, the dye absorption maxima ($\lambda$max) are too hypsochromically shifted (that is, shifted to the blue or short wavelength side of the visible spectrum) and the absorption spectra are too broad with considerable amounts of undesirable blue and green absorptions and often lack sufficient stability toward light fading. Thus, these couplers are not as desired for use in color papers.

The hue of a dye is a function of both the shape and the position of its spectral absorption band. Traditionally, the cyan dyes used in color photographic papers have had nearly symmetrical absorption bands centered in the region of 620 to 680 nm, typically 630 to 660 nm, and more often 635 to 655 nm. Such dyes have rather large amounts of unwanted absorption in the green and blue regions of the spectrum.

More desirable would be a dye whose absorption band is asymmetrical in nature and biased towards the green region, that is, with a steep slope on the short wavelength side. Such a dye would suitably peak at a shorter wavelength than a dye with symmetrical absorption band, but the exact position of the desired peak depends on several factors including the degree of asymmetry and the shapes and positions of the absorption bands of the magenta and yellow dyes with which it is associated.

Recently, Lau et al., in U.S. Pat. No. 5,686,235, describe a particular class of cyan dye-forming coupler that has been shown to improve thermal stability and hue, particularly with decreased absorption in side bands and an absorption band that is asymmetrical in nature. However, it has been found that dispersions of these couplers are difficult to prepare free of crystalline material, and are not phase stable with time in cold storage. Other related patents are U.S. Pat. Nos. 5,047,314, 5,047,315, 5,057,408, and 5,162,197.

The above mentioned couplers of U.S. Pat. No. 5,686,235 contain an aryl sulfone function in the ballast portion of the molecule. It is believed this functional group assisted in generating a favorable conformation of the dye in order to obtain the desired narrow spectral shape. One drawback with these couplers from a manufacturing point of view is the extended syntheses required in constructing the aryl sulfone ballast.

It would be desirable to have a cyan dye-forming coupler having hue properties comparable to the arylsulfone type of Lau but without the synthesis difficulties associated with the aryl sulfone.

SUMMARY OF THE INVENTION

The invention provides a photographic element comprising a light-sensitive silver halide emulsion layer having associated therewith a cyan dye-forming coupler represented by Formula (I):

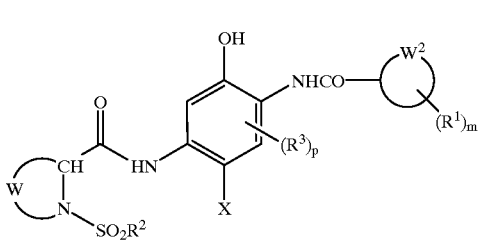

(I)

wherein:
each $R^1$ and $R^3$ is an independently selected substituent, m is 0 to 5, and p is 0 to 2;
X is hydrogen or a coupling-off group;
W and $W^2$ represent the atoms necessary to complete rings; and
$R^2$ is an alkyl or aryl group.

The invention also provides a method of forming an image in an element of the invention and a novel coupler compound. The invention element provides a cyan dye of improved ease of synthesis while retaining the hue advantages of the prior art.

DETAILED DESCRIPTION OF THE INVENTION

The invention is as generally described in the Summary of the Invention.

The hetero ring in the 5-position of the phenol is suitably a 4 or 5-membered ring. A five membered ring is conveniently employed. One embodiment employs three $CH_2$ groups to complete the ring (n=3 in Formula (II)).

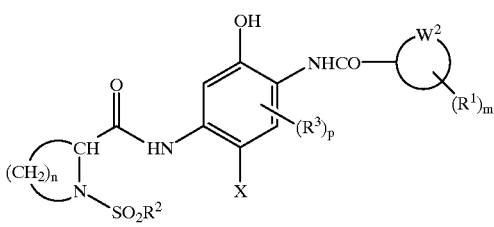

(II)

The group $R^2$ is suitable an alkyl or aryl group. Desirable is an alkyl group of 4 to 18 carbon atoms, such as a dodecyl group, or a phenyl group.

Typically, p=0 and m is 1 to 3. It is generally desirable that at least one group $R^1$ is an electron withdrawing group having a positive Hammett's sigma value. Suitable such groups include chloro, sulfonyl, sulfonamide, sulfamoyl, and carboxy groups.

X may be hydrogen or any coupling-off group as described hereinafter.

Embodiments also provide other advantageous properties such as coupler and dye stability and reactivity.

The following are specific examples of couplers useful in the invention:

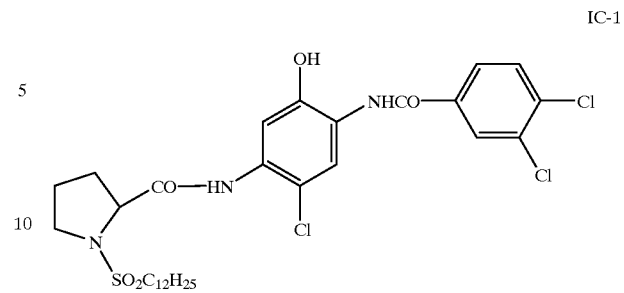

IC-1

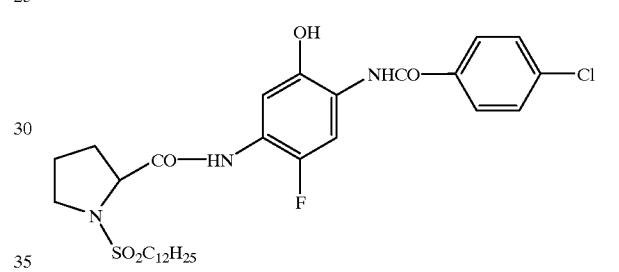

IC-2

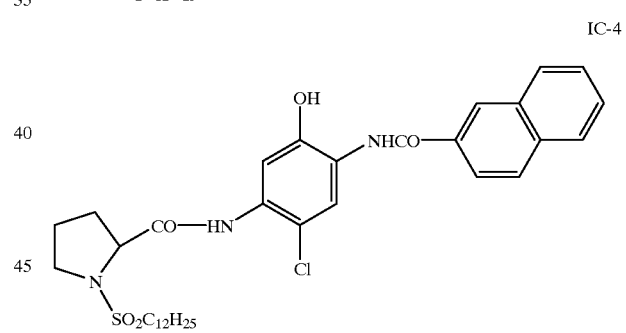

IC-3

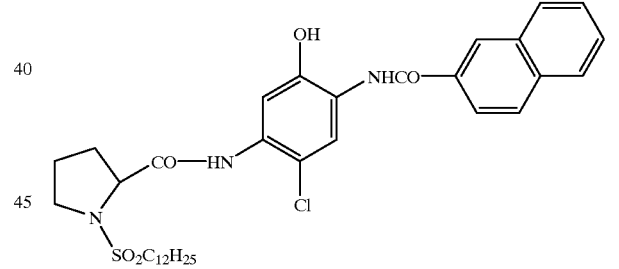

IC-4

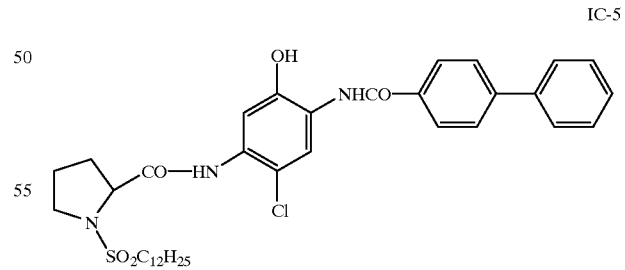

IC-5

-continued
IC-6
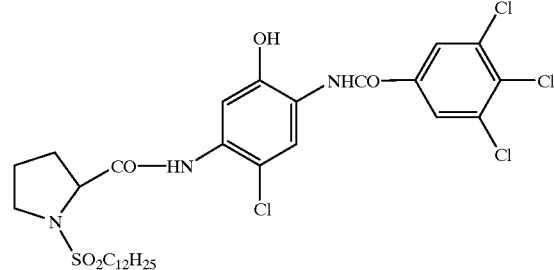
IC-7
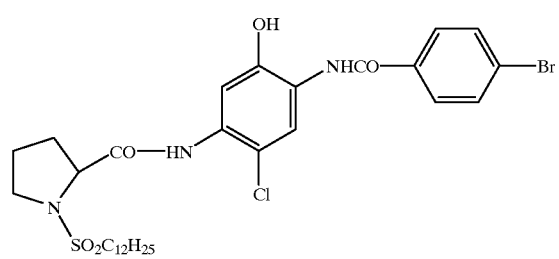
IC-8
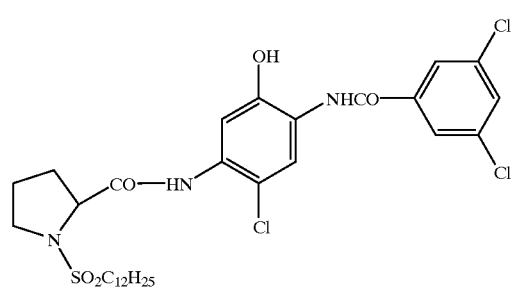
IC-9
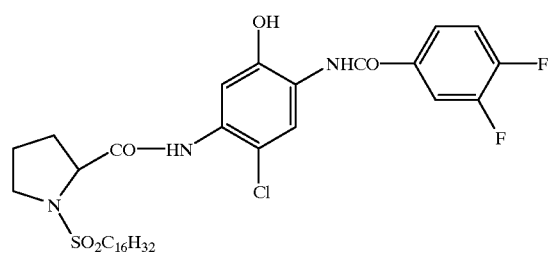
IC-10
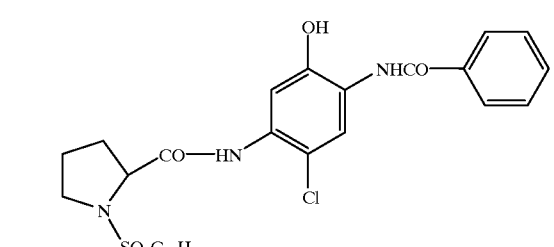
-continued
IC-11
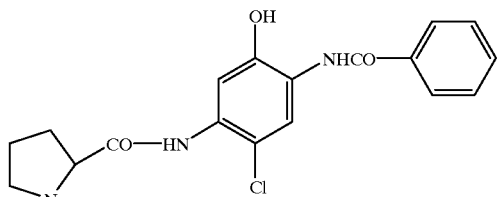
IC-12
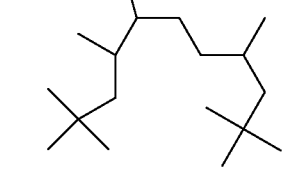
IC-13
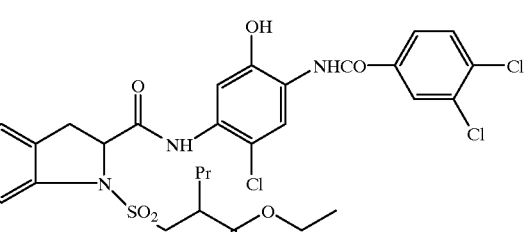
IC-14
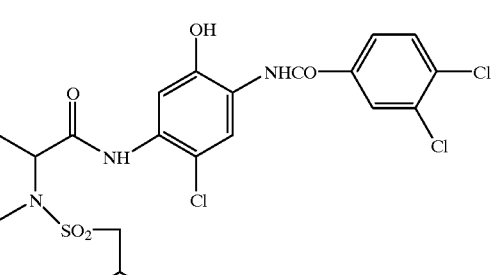
IC-15
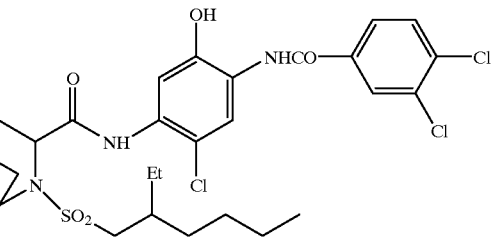

-continued

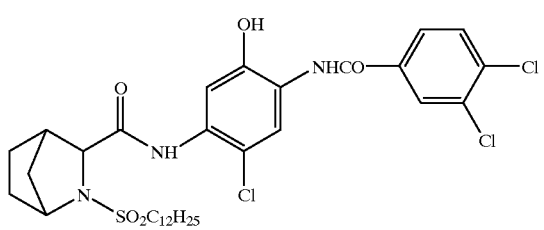

IC-16

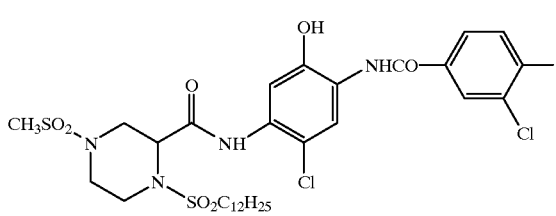

IC-17

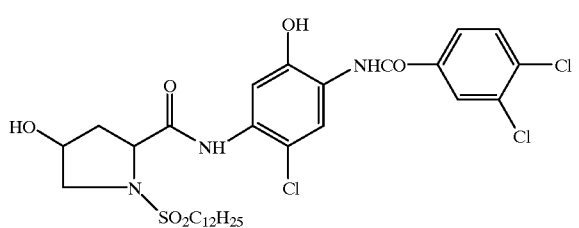

IC-18

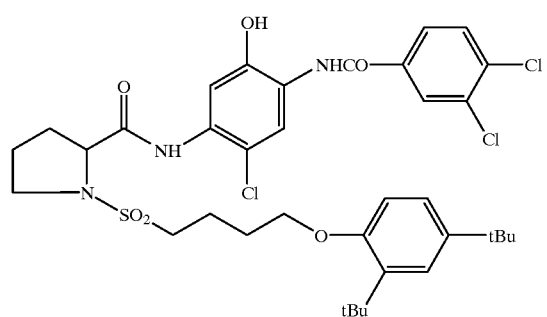

IC-19

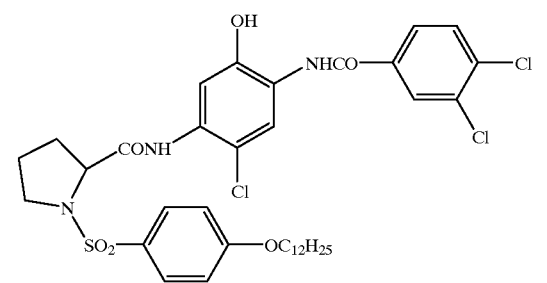

IC-20

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-( 2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in the component molecule. Representative ballast groups include substituted or unsubstituted alkyl or aryl groups containing 8 to 40 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 40 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire P010 7DQ, ENGLAND, or as described in Hatsumi Kyoukai Koukai Gihou No. 94-6023, published Mar. 15, 1994, available from the Japanese Patent Office, the contents of which are incorporated herein by reference.

In the following discussion of suitable materials for use in the emulsions and elements of this invention, reference will be made to *Research Disclosure,* September 1996, Item 38957, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. Certain desirable photographic elements and processing steps are described in *Research Disclosure,* Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl such as oxazolidinyl or hydantoinyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp.156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201;EPO 0 271 323;EPO 0 295 632;EPO 0 307 927;EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp.126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629.

Typically, couplers are incorporated in a silver halide emulsion layer in a mole ratio to silver of 0.1 to 1.0 and generally 0.1 to 0.5. Usually the couplers are dispersed in a high-boiling organic solvent in a weight ratio of solvent to coupler of 0.1 to 10.0, typically 0.1 to 2.0 and usually 0.1 to 0.6, although direct dispersions are sometimes employed.

The invention materials may also be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097, 140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

It is contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al U.S. Pat. Nos. 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in *Research Disclosure* XVIII-B(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3'15" or less and desirably 90 or even 60 seconds or less.

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The print may then be processed to form a positive reflection image using, for example, the Kodak RA-4 process as generally described in PCT WO 87/04534 or U.S. Pat. No. 4,975,357. Color projection prints may be processed, for example, in accordance with the Kodak ECP-2 process as described in the H-24 Manual. Similarly, back-lit image transparencies may be prepared for display purposes. Color print development times are typically 90 seconds or less and desirably 45 or even 30 seconds or less.

The above emulsions are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride,
4-amino-3-methyl-N,N-diethylaniline hydrochloride,
4-amino-3-methyl-N-ethyl-N-(2-methanesulfonamido-ethyl)aniline sesquisulfate hydrate,
4-amino-3-methyl-N-ethyl-N-(2-hydroxyethyl)aniline sulfate,
4-amino-3-(2-methanesulfonamido-ethyl)-N,N-diethylaniline hydrochloride and
4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

Synthesis

The cyan couplers of this invention can be prepared by reacting the desired m-aminophenol (syntheses described in U.S. Pat. No. 5,686,235) with the appropriate ballasted nitrogen heterocyclic acid chloride as illustrated by the synthesis of IC-1.

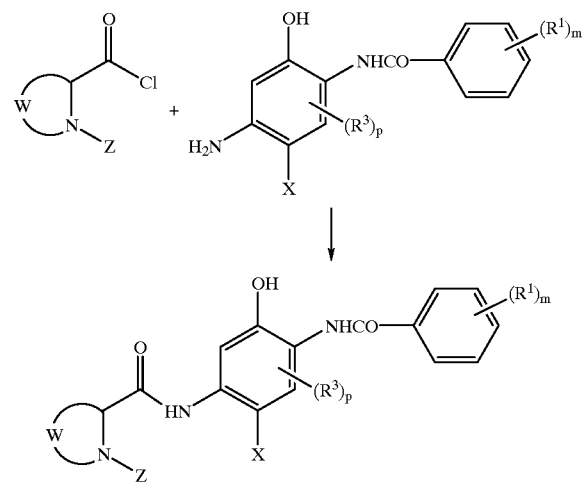

The heterocycle acid chloride is prepared as follows:

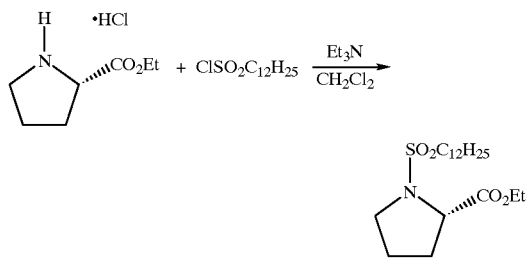

Proline ethyl ester (Aldrich; 10 g, 60.3 mmol) was dissolved in dichloromethane (200 ml) with stirring under nitrogen. The solution was cooled in an acetone/ice bath and triethyl amine (12.2 g, 120.6 mmol) was added followed by a dropwise addition of the sulfonyl chloride (16.2 g, 60.3 mmol) dissolved in dichloromethane (100 ml). After 3 hours, the reaction mixture was filtered and the filtrate freed of solvent under vacuum. The cream colored solid isolated from solvent removal was stirred in dilute HCl/ice water (200 ml) for a few minutes, filtered and the solid washed with cold water. Air drying on the filter afforded 17.6 g of white solid. This solid was combined with another run and passed through a short plug of silica gel with dichloromethane. NMR (CDCl$_3$),: 0.8–0.95 (t, 3H); 1.2–1.5 (m, 22H); 1.65–1.9 (m, 2H); 1.9–2.35 (m, 6H); 3.05–3.15 (t, 2H); 3.4–3.65 (m, 2H); 3.75 (s, 3H); 4.5–4.55 (m, 1H). Mp.: 40–41° C.

The proline sulfonamide (24 g, 66.4 mmol) was dissolved in tetrahydrofuran (100 ml) and methanol (100 ml) with stirring and 50% NaOH (0.166 mol NaOH) was added in portions, followed by the addition of water (10 ml). After 3 hours, the reaction mixture was freed of solvent under vacuum to afford a white solid. Dilute HCl/ice water was added to the solid with stirring until the mixture was acidic. After stirring for a few minutes, the solid was isolated by filtration and washed with ice water. Air drying on the filter and in a vacuum oven at 40° afforded 22.6 g (98%) of the desired product. NMR (CDCl$_3$) revealed the removal of the methyl ester singlet at 3.75δ.

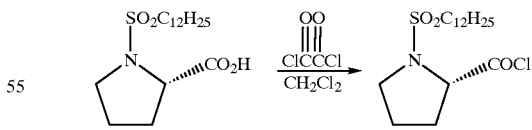

The proline sulfonamide acid (22.5 g, 64.7 mmol) was dissolved in dichloromethane (300 ml) and oxalyl chloride (10.6 g, 84.2 mmol) was added followed by a few drops of DMF. After stirring for 8 hours, solvent was removed from the reaction under vacuum. Dichloromethane (200 ml) was again added and removed under vacuum to afford the product as a pale yellow solid (23.6 g). NMR revealed the desired shift in the multiplet for the proton on the carbon alpha to the acid chloride from δ4.5–4.55 to 4.8–4.9.

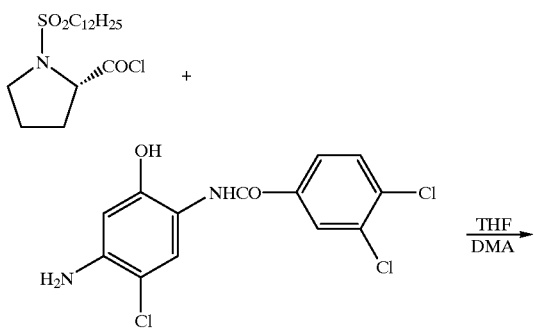

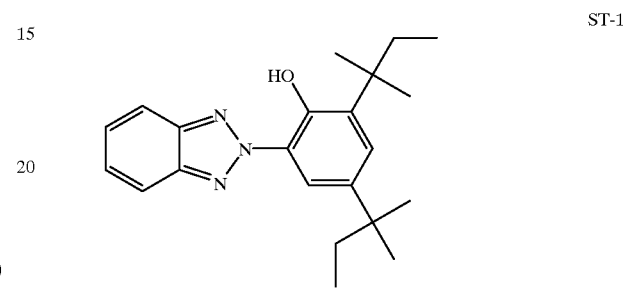

The proline acid chloride (23 g, 62.8 mmol) in THF (140 ml) was added dropwise to a cold suspension of coupler aniline (19.78 g, 59.6 mmol) and dimethylaniline (7.61 g, 62.8 mmol) in THF (400 ml). After addition of acid chloride was complete (30 min.), the ice bath was removed and the reaction was allowed to stir an additional 4 hours. Most of the THF was removed under vacuum and the resultant mixture was poured into dilute HCl/ice water (1.5 L). After stirring for 30 min., the light tan solid was isolated by filtration and washed with water (3×'s). Air drying afforded a light tan solid (40.8 g) that was chromatographed on silica gel with 95:5; $CH_2Cl_2$:ether. The resultant solid was stirred in ether, filtered and dried to afford 10 g of the desired product as a cream colored solid (mp. 152–154°). An additional amount of product (16.7 g) was obtained by combining all less pure fractions and recrystallizing from MeOH. Mass Spec [electron spray; m/e=660 (P–1)].

PHOTOGRAPHIC EXAMPLES

Preparation of Photographic Elements

Coupler IC-1, stabilizer ST-1, and coupler solvent dibutyl sebacate were dispersed in aqueous gelatin in the following manner. Coupler IC-1 (0.658 g, $8.4 \times 10^{-4}$ mole) and stabilizer ST-1 (0.444 g, $1.26 \times 10^{-3}$ mole) were dissolved in dibutyl sebacate (0.658 g) and ethyl acetate (1.975 g). The mixture was heated to effect solution. After adding a solution of aqueous gelatin (22.58 g, 11.6% solution), surfactant Alkanol XC (trademark of E. I. Dupont Co.) (2.60 g, 10% solution), and water to make a total of 39.31 grams, the mixture was dispersed by passing it three times through a Gaulin homogenizer. This dispersion was used in the preparation of the photographic elements.

Dispersions containing the couplers shown for elements in Table 1 were prepared in a similar manner except that the IC-1 was omitted and coupler indicated was used in its place The photographic elements were prepared as follows: On a gel-subbed, polyethylene-coated paper support were coated the following layers:

First Layer

An underlayer containing 3.23 grams gelatin per square meter.

Second Layer

A photosensitive layer containing (per square meter) 2.15 grams total gelatin, an amount of red-sensitized silver chloride emulsion containing 0.194 grams silver; the dispersion containing $5.38 \times 10^{-4}$ mole of the coupler indicated in Table 1; and 0.043 gram surfactant Alkanol XC (in addition to the Alkanol XC used to prepare the coupler dispersion Third Layer A protective layer containing (per square meter) 1.40 grams gelatin, 0.15 gram bis(vinylsulfonyl)methyl ether, 0.043 gram Alkanol XC, and $4.40 \times 10^{-6}$ gram tetraethylammonium perfluorooctanesulfonate.

ST-1

Preparation of Processed Photographic Examples

Processed samples were prepared by exposing the coatings through a step wedge and processing as follows:

| Process Step | Time (min.) | Temp. (C) |
| --- | --- | --- |
| Developer | 0.75 | 35.0 |
| Bleach-Fix | 0.75 | 35.0 |
| Water wash | 1.50 | 35.0 |

The processing solutions used in the above process had the following compositions (amounts per liter of solution):

| Developer | |
| --- | --- |
| Triethanolamine | 12.41 g |
| Blankophor REU (trademark of Mobay Corp.) | 2.30 g |
| Lithium polystyrene sulfonate | 0.09 g |
| N,N-Diethylhydroxylamine | 4.59 g |
| Lithium sulfate | 2.70 g |
| 4-amino-3-methyl-N-ethyl-N-(2-methansulfonamidoethyl)-aniline sesquisulfate hydrate | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| pH adjusted to 10.4 at 26.7 C | |
| Bleach-Fix | |
| Solution of ammonium thiosulfate | 71.85 g |
| Ammonium sulfite | 5.10 g |
| Sodium metabisulfite | 10.00 g |
| Acetic acid | 10.20 g |
| Ammonium ferric ethylenediaminetetra acetate | 48.58 g |
| Ethylenediaminetetraacetic acid | 3.86 g |
| pH adjusted to 6.7 at 26.7 C | |

The wavelength of maximum absorption was recorded as the "λmax." As a measure of the sharpness of the curve on the left (short wavelength) side of the absorption band the "left bandwidth" (LBW) was obtained by subtracting from λmax the wavelength at the left side of the absorption band where the density is 0.50 λmax. A lower value of LBW indicates a reduction in the unwanted green absorption and is thus desirable.

Comparison coupler C-1 is a state of the art coupler used in color negative film but not in print applications. Comparison C-2 is an example described in U.S. Pat. No. 5,686,235 but which presents concerns regarding ease of synthesis. As can be seen from Table 1, spectral data for the coupler useful in the invention, IC-1, is very similar to that for C-2 shown in U.S. Pat. No. 5,686,235, but this coupler does not present the synthesis problems of the prior art. It is clear, however, that the $\lambda_{max}$ and LBW values for the two compounds useful in the invention compared to comparatives C-1, C-3, C-4, and C-5 are desirably more hypsochromic and narrower in left-half bandwidth.

TABLE 1

| Coupler | Type | $\lambda_{max}$ nm | LBW nm |
|---|---|---|---|
| C-1 | Comp | 680 | 90 |
| C-2 | Comp | 626 | 43 |
| C-3 | Comp | 641 | 98 |
| C-4 | Comp | 640 | 86 |
| C-5 | Comp | 639 | 80 |
| IC-1 | Inv | 625 | 47 |
| IC-20 | Inv | 627 | 47 |

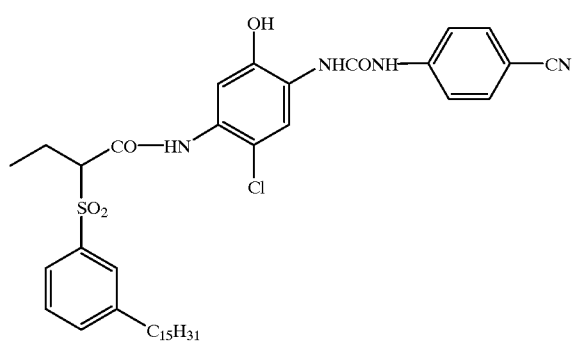

C-1

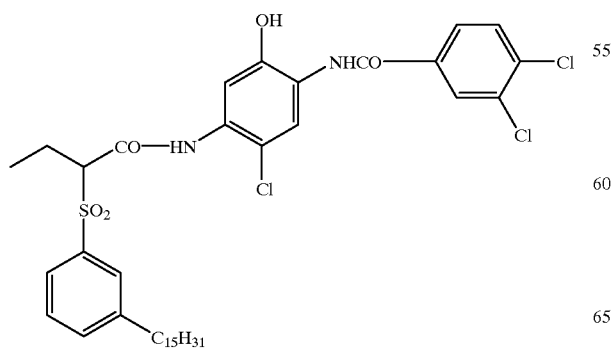

C-2

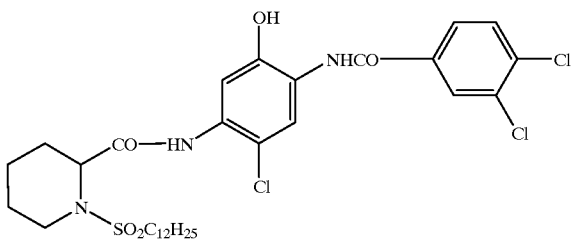

C-3

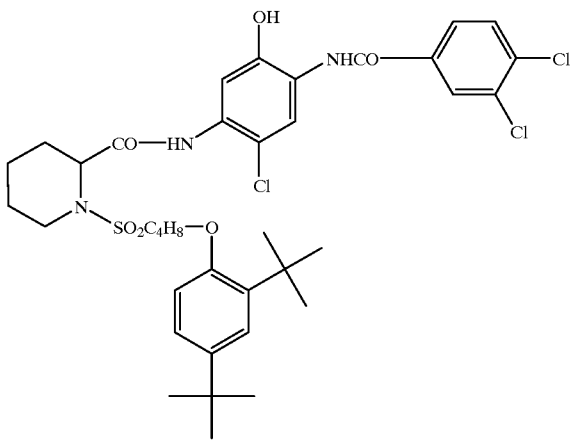

C-4

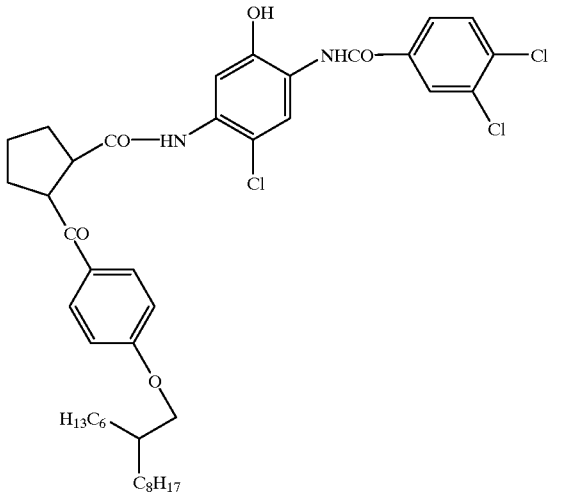

C-5

$$CH_3(CH_2)_7CH=CH(CH_2)_8OH \qquad S\text{-}1$$

The entire contents of the patents and other publications cited in this specification are incorporated herein by reference.

What is claimed is:

1. A photographic element comprising a light-sensitive silver halide emulsion layer having associated therewith a cyan dye-forming coupler represented by Formula (I):

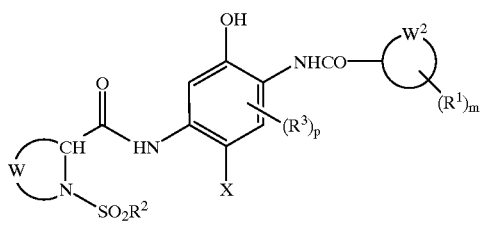

wherein:
  each $R^1$ and $R^3$ is an independently selected substituent, m is 0 to 5, and p is 0 to 2;
  X is hydrogen or a coupling-off group;
  W and $W^2$ represent the atoms necessary to complete rings; and
  R is an alkyl or aryl group.

2. The photographic element of claim 1 wherein the coupler represented by Formula (I) is be represented by Formula (II):

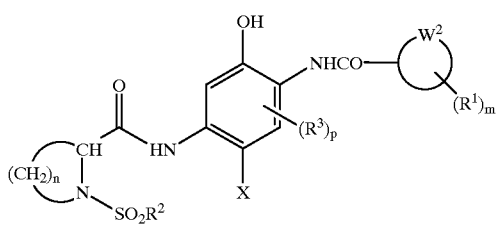

wherein n is 2 or 3.

3. The element of claim 2 wherein n is 3.
4. The element of claim 2 wherein $R^2$ is an aryl group.
5. The element of claim 2 wherein $R^2$ is an alkyl group.
6. The element of claim 5 wherein the alkyl group contains from 4 to 18 carbon atoms.
7. The element of claim 6 wherein n is 3.
8. The element of claim 7 wherein the alkyl group is a dodecyl group.
9. The element of claim 1 wherein m is at least 1.
10. The element of claim 1 wherein m is at least 2.
11. The element of claim 1 wherein p is 0.
12. The element of claim 1 wherein X is hydrogen.
13. The element of claim 1 wherein X is selected from halogen, aryloxy, and arylthio, and an N-hetero ring group.
14. The element of claim 1 wherein the coupler of Formula (I) is in the silver halide emulsion layer.
15. The element of claim 2 wherein n is 3, m is at least 2, and p is 0, and $R^2$ is an alkyl group or a phenyl group.
16. The element of claim 15 wherein m is at least 2 and at least two $R^1$ groups are chloro.
17. The element of claim 16 wherein the two chloro groups are in the 3- and 4-positions of the $W^2$ ring.
18. The element of claim 1 wherein the $W^2$ ring is a phenyl ring.
19. A process for forming an image in an element as described in claim 1 after the element has been imagewise exposed, comprising containing the element with a color-developing compound.
20. The element of claim 18 wherein the color-developing compound is a paraphenylene diamine.

* * * * *

UNITED STATES PATENT AND TRADEMARK OFFICE
CERTIFICATE OF CORRECTION

PATENT NO. : 6,190,852 B1
DATED : February 20, 2001
INVENTOR(S) : Albert J. Mura, Raymond P. Scaringe and John W. Harder It is certified that error appears in the above-identified patent and that said Letters Patent is hereby corrected as shown below:

Column 21,
Line 19, insert -- $R^2$ -- in place of "R".

Signed and Sealed this

Twenty-third Day of April, 2002

Attest:

Attesting Officer

JAMES E. ROGAN
Director of the United States Patent and Trademark Office